(12) United States Patent
Shimago et al.

(10) Patent No.: US 6,376,469 B1
(45) Date of Patent: Apr. 23, 2002

(54) CRYSTALLINE AMRUBICIN HYDROCHLORIDE

(75) Inventors: Kozo Shimago, Sanda; Yuko Uenishi, Toyonaka, both of (JP)

(73) Assignee: Sumitomo Pharmaceuticals Company, Limited, Osaka (JP)

( * ) Notice: Subject to any disclaimer, the term of this patent is extended or adjusted under 35 U.S.C. 154(b) by 0 days.

(21) Appl. No.: 09/555,066

(22) PCT Filed: Nov. 25, 1998

(86) PCT No.: PCT/JP98/05296
  § 371 Date: May 24, 2000
  § 102(e) Date: May 24, 2000

(87) PCT Pub. No.: WO99/28331
  PCT Pub. Date: Jun. 10, 1999

(30) Foreign Application Priority Data

Nov. 28, 1997 (JP) ............................................. 9-343858

(51) Int. Cl.⁷ ......................... A61K 31/70; C07H 15/24
(52) U.S. Cl. ............................................ 514/34; 536/6.4
(58) Field of Search ............................... 314/34; 536/6.4

(56) References Cited

U.S. PATENT DOCUMENTS

| | | | |
|---|---|---|---|
| 4,673,668 A * | 6/1987 | Ishizumi et al. ............... | 514/34 |
| 4,952,566 A * | 8/1990 | Sakamaki et al. ............ | 514/34 |
| 6,184,365 B1 * | 2/2001 | Takeuchi et al. ............ | 536/17.2 |
| 6,187,758 B1 * | 2/2001 | Portello et al. ............... | 514/34 |

FOREIGN PATENT DOCUMENTS

| | | |
|---|---|---|
| EP | A107486 | 5/1984 |
| EP | A302729 | 2/1989 |

OTHER PUBLICATIONS

Kikuo Ishizumi et al., J. Org. Chem., 1987, 52, pp. 4477–4485, Stereospecific Total Synthesis of 9–Aminoanthracyclines: . . . .

* cited by examiner

*Primary Examiner*—Deborah C. Lambkin
(74) *Attorney, Agent, or Firm*—Birch, Stewart, Kolasch & Birch, LLP

(57) ABSTRACT

β-Type crystalline amrubicin hydrochloride having a powder X-ray diffraction pattern having average values of diffraction angle(2θ) and relative intensity as given in the following table:

| diffraction angle(2θ) (average value) | relative intensity(%) (average value) |
|---|---|
| 6.3 | 100 |
| 6.7 | 56 |
| 10.1 | 44 |
| 15.3 | 36 |
| 20.3 | 56 |
| 25.6 | 37 |
| 26.5 | 61 |
| 26.9 | 52 | has excellent thermal stability and is used in production of freeze-dried formulations.

12 Claims, 2 Drawing Sheets

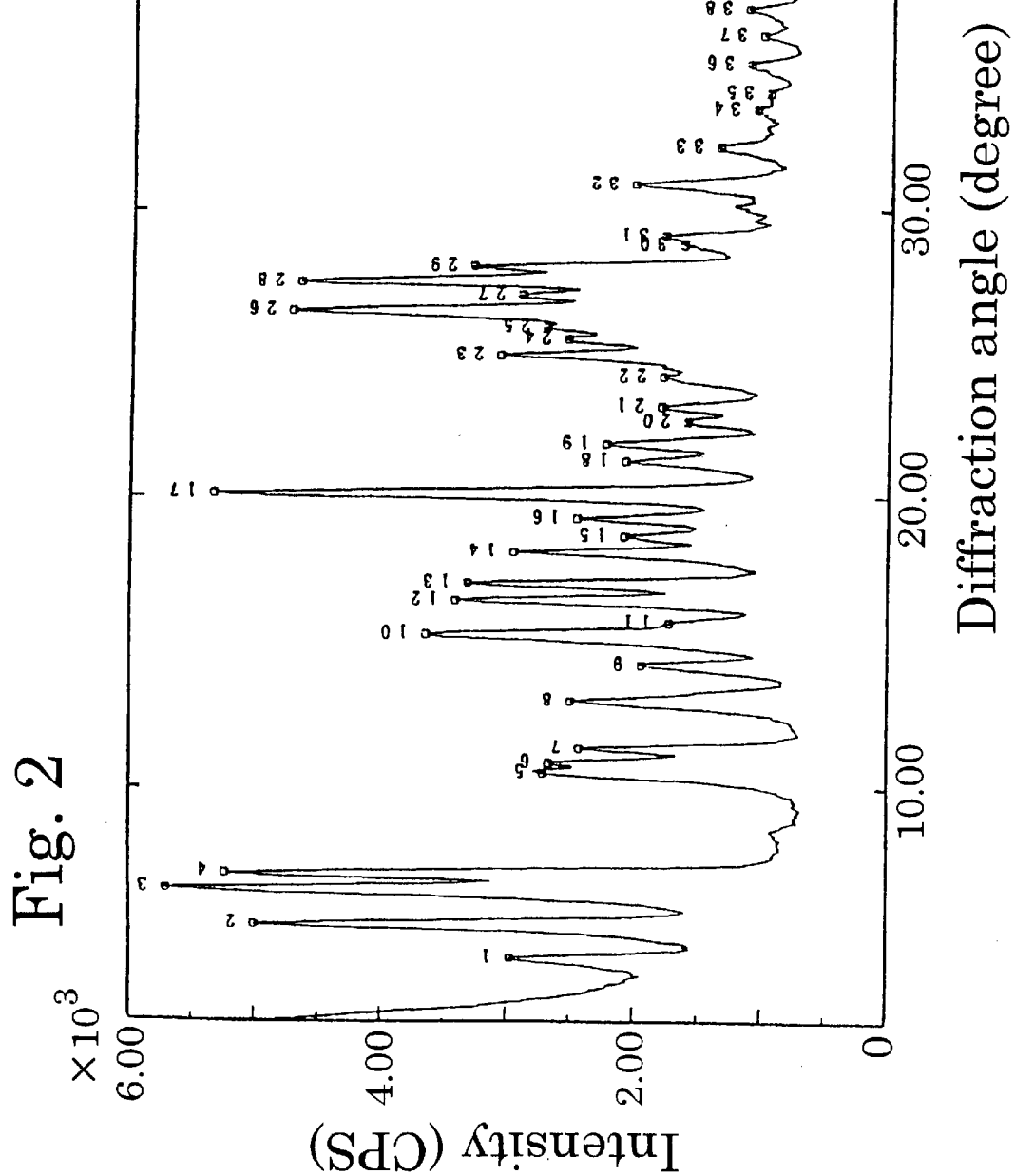

CRYSTALLINE AMRUBICIN HYDROCHLORIDE

This application is the national phase under 35 U.S.C. §371 of PCT International Application No. PCT/JP98/05296 which has an International filing date of Nov. 25, 1998, which designated the United States of America.

TECHNICAL FIELD

The present invention relates to a crystalline form of amrubicin hydrochloride which is useful as a drug.

BACKGROUND OF THE INVENTION

Japanese Patent KOKOKU(Examined) 3-5397 and U.S. Pat. No. 4,673,668 disclose the preparation of (7S,9S)-9-acetyl-9-amino-7-[(2-deoxy-β-D-erythro-pentapyranosyl)oxy]-7,8,9, 10-tetrahydro-6,11-dihydroxy-5,12-naphthacenedione hydrochloride and its usage as a cancer-chemotherapeutical agent, which is referred to as "amrubicin hydrochloride" hereinafter and is represented by the formula:

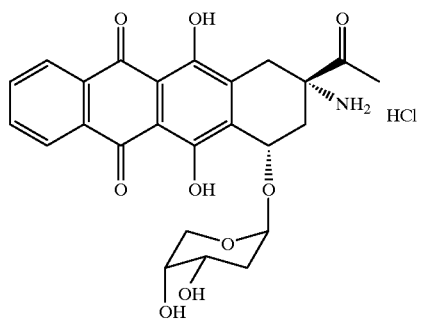

However, these Patents do not specifically disclose thermally stable crystalline amrubicin hydrochloride.

Japanese Patent 2,603,480 and U. S. Pat. No. 4,952,566 disclose stable preparations of amrubicin hydrochloride containing agents such as L-cysteine. These patents disclose preparations for stabilized injection, but do not disclose the stabilization of amrubicin hydrochloride itself as a medicine or a bulk drug.

DISCLOSURE OF THE INVENTION

The inventors of the present invention have intensively carried out research on the crystalline forms of amrubicin hydrochloride, and found that a specific crystal form of amrubicin hydrochloride which is referred to as "β-type crystalline amrubicin hydrochloride" hereinafter, has excellent thermal stability. Thus, the present invention has been accomplished.

Accordingly, the objects of the present invention are as follows:

[1] A crystalline amrubicin hydrochloride having a powder X-ray diffraction pattern as given in Table 1

TABLE 1

| diffraction angle(2θ) (average value) | relative intensity(%) (average value) |
| --- | --- |
| 6.3 | 100 |
| 6.7 | 56 |

TABLE 1-continued

| diffraction angle(2θ) (average value) | relative intensity(%) (average value) |
| --- | --- |
| 10.1 | 44 |
| 15.3 | 36 |
| 20.3 | 56 |
| 25.6 | 37 |
| 26.5 | 61 |
| 26.9 | 52 |

[2] A process of preparing a crystalline amrubicin hydrochloride according to [1] comprising crystallizing amrubicin hydrochloride at a temperature of 15° C. or above.

[3] A process according to [2] comprising crystallizing amrubicin hydrochloride from a mixture of (a) hydrophilic organic solvent and (b) a solution of amrubicin hydrochloride in water or a mixture of water and hydrophilic organic solvent, at a temperature of 15° C. or above.

[4] A process according to [2] comprising:
  (1) dissolving amrubicin hydrochloride in water or a mixture of water and hydrophilic organic solvent;
  (2) adjusting the pH of the solution to a value of from pH 1.5 to pH 4;
  (3) crystallizing amrubicin hydrochloride by adding the solution to hydrophilic organic solvent at a temperature of 15° C. or above, preferably up to 50° C.

[5] A process according to [2], [3] or [4], wherein the crystallization temperature is 22° C. to 40° C.

[6] A process according to [3], [4] or [5], wherein the hydrophilic organic solvent (a) is acetone, isopropanol or acetonitrile.

[7] A process of preparing a freeze-dried preparation of amrubicin hydrochloride, comprising dissolving crystalline amrubicin hydrochloride according to [1] in water, and freeze-drying the dissolved amrubicin hydrochloride.

[8] A process according to [7] comprising:
  (1) dissolving crystalline amrubicin hydrochloride according to [1] and L-cysteine or a salt thereof in water;
  (2) adjusting the pH of the solution to a value of from pH 2 to pH 5; and
  (3) freeze-drying the dissolved amrubicin hydrochloride.

[9] Use of crystalline amrubicin hydrochloride according to [1] in the production of a freeze-dried pharmaceutical formulation.

[10] A crystalline amrubicin hydrochloride according to [1] for use in the treatment of the human or animal body by therapy.

[11] Use of a crystalline amrubicin hydrochloride according to [1] in the preparation of a medicament comprising a freeze-dried form thereof for use in the treatment of cancer by injection of said freeze-dried form into a patient in need of such treatment.

[12] A pharmaceutical composition comprising a crystalline amrubicin hydrochloride according to [1] and a pharmaceutically acceptable carrier.

[13] A method of treating cancer comprising administrating to a person in need thereof, a freeze-dried preparation of amrubicin hydrochloride prepared according to [7] or [8].

[14] A method of treating cancer comprising administrating to a person in need thereof, a pharmaceutical composition according to [12].

BRIEF DESCRIPTION OF THE DRAWINGS

FIG. 2 shows a powder X-ray diffraction spectrum of α-type crystalline amrubicin hydrochloride obtained in Reference Example 1.

DETAILED DESCRIPTION OF THE INVENTION

Figure 1:
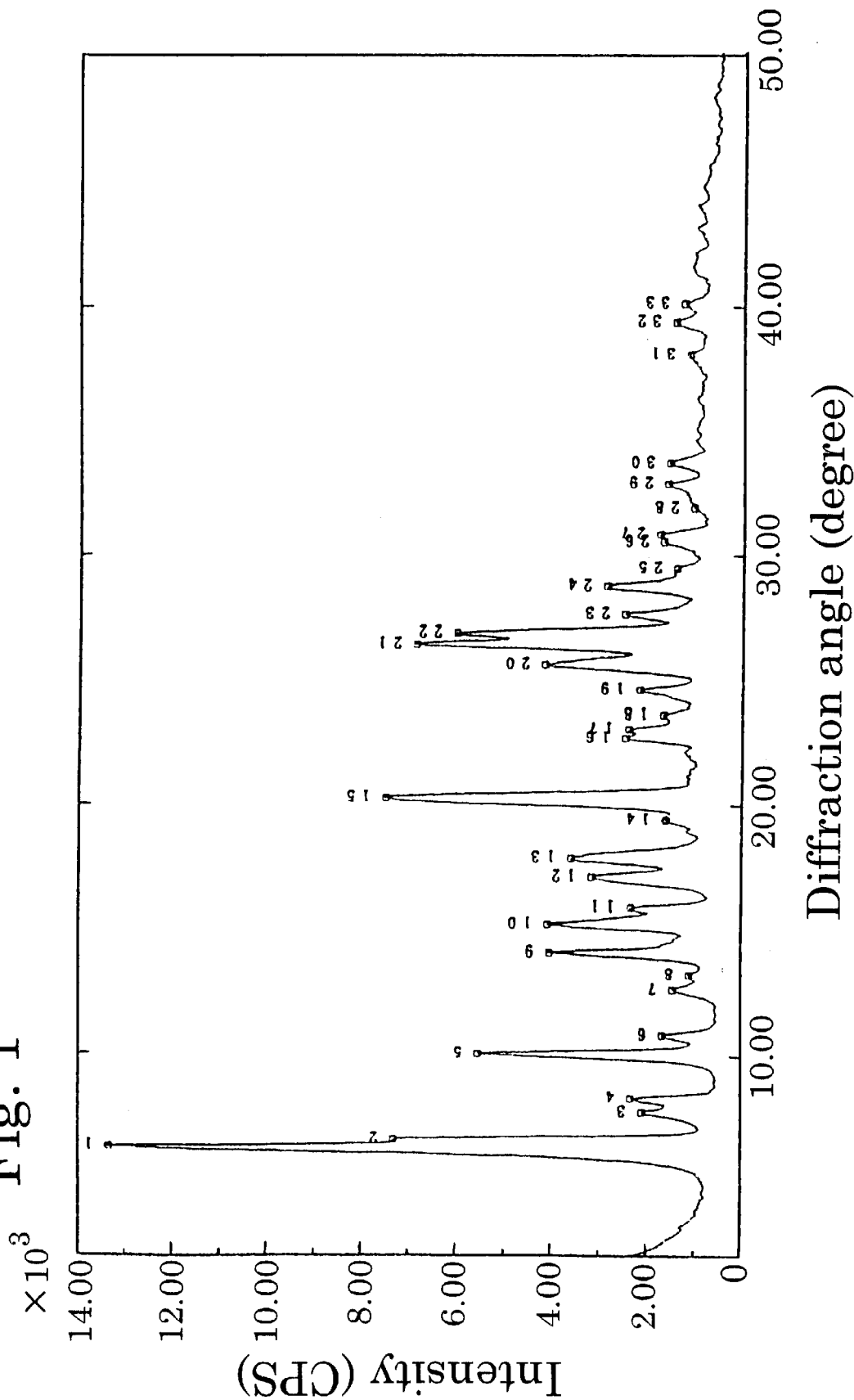
FIG. 1 shows a powder X-ray diffraction spectrum of β-type crystalline amrubicin hydrochloride obtained in Example 1.

β-Type crystalline amrubicin hydrochloride of the present invention can be produced by crystallizing amrubicin hydrochloride from a solvent which can hardly or slightly dissolve amrubicin hydrochloride such as a mixture of water and hydrophilic organic solvent, at a temperature of 15° C. or above. Specifically, β-type crystalline amrubicin hydrochloride can be produced by crystallizing amrubicin hydrochloride by mixing (a) a hydrophilic organic solvent and (b) a solution of amrubicin hydrochloride in a mixture of water and hydrophilic organic solvent, at a temperature of 15° C. or above.

Prior to addition to the hydrophilic organic solvent, the amrubicin hydrochloride is present in solution in water or a mixture of water with hydrophilic organic solvent as described above (hereafter referred to as "solvent dissolving amrubicin hydrochloride"). The amount of water in mixtures of water and hydrophilic organic solvent is, for example, at least 1 part by weight, preferably 1 to 3 parts by weight per part of the hydrophilic organic solvent.

The amount of the solvent dissolving amrubicin hydrochloride is, for example, 5 to 50 parts by weight, preferably 10 to 30 parts by weight per part of amrubicin hydrochloride.

Preferably the pH of the solution of amrubicin hydrochloride is adjusted to a value of from pH 1.5 to pH 4, more preferably from pH 2 to pH 3 by adding an acid thereto. Suitable acids include hydrochloric acid and straight or branched $C_1-C_6$ alkanoic acids such as formic acid, acetic acid and propionic acid. A preferred example is acetic acid.

In one embodiment the solution of amrubicin hydrochloride is prepared by dissolving amrubicin in dilute hydrochloric acid.

The solution of amrubicin hydrochloride may be prepared in advance and preserved at a temperature of 0 to 20° C., preferably 0 to 5 ° C.

Suitable hydrophilic organic solvents include inert organic liquids such as ketones, alcohols, nitrites and ethers and a mixture thereof. Ketone solvents include straight or branched $C_3-C_6$ ketones, such as acetone, 2-butanone, 3-pentanone and 4-methyl-2-pentanone. A preferred example is acetone. Alcohol solvents include straight or branched $C_1-C_6$ alcohols such as methanol, ethanol, 1-propanol and 2-propanol. A preferred example is 2-propanol. Nitrile solvents include straight or branched $C_2-C_6$ nitrites such as acetonitrile and propionitrile. A preferred example is acetonitrile. Ether solvents include straight or branched $C_4-C_6$ ethers such as diethyl ether, methyl t-butyl ether and cyclic ethers having 5 or 6 membered ring such as tetrahydrofuran and 1,4-dioxane.

The hydrophilic organic solvent (a) may be the same as or different from that in the solvent dissolving amrubicin hydrochloride. The amount of the hydrophilic organic solvent mixed with the solution of amrubicin hydrochloride may be, for example, 1 to 100 parts by weight, preferably 5 to 50 parts by weight, more preferably 10 to 20 parts by weight per part of the solution of amrubicin hydrochloride. The temperature of the hydrophilic organic solvent with which the solution of amrubicin hydrochloride is mixed may be, for example, 15 to 50° C., more preferably 22 to 40° C. What is most important is that the solution from which the amrubicin hydrochloride is crystallized is held at a temperature of 15° C. or more during the crystallization.

The period of time for mixing the solution of amrubicin hydrochloride and the hydrophilic organic solvent is not limited, but preferably it is in the range of 10 minutes to 1 day.

After mixing, the mixture is preferably preserved at an approximately constant temperature for a period preferably of 30 minutes to 1 day, more preferably for 1 to 5 hours to accomplish the crystallization. Seed crystals of β-type crystalline amrubicin hydrochloride may be added into the mixture to accelerate cystallization.

The thus obtained crystals may be recovered by common procedures, for example, by filtration under reduced pressure or by centrifugal filtration, followed by drying the crystals, to obtain β-type crystalline amrubicin hydrochloride of the present invention.

β-Type crystalline amrubicin hydrochloride may be also prepared by subjecting another form of crystalline amrubicin hydrochloride or a mixture of several forms of crystalline amrubicin hydrochloride to the procedure as described above.

Occasionally, the β-type crystalline amrubicin hydrochloride bears the hydrophilic organic solvent used in crystallization. In that case, the organic solvent may be removed from the crystals, if desired, by moistening the crystals and drying the moistened crystals again.

The moistening treatment can be carried out in a conventional manner, for example, by letting the crystals stand under moistened air at 0 to 50° C., preferably 10 to 30° C. The moistened air has a relative humidity of 50 to 95%, more preferably 80 to 90% RH. The pressure of the moistened air is not limited, but usually 1 mmHg to 1 atm, preferably 10 mmHg to 200 mmHg. The moistening treatment can be monitored by measuring the amount of organic solvent in the crystals. Usually, the moistening may be completed in about 1 to 24 hours.

The drying treatment can be carried out in a conventional manner, for example by subjecting the moistened crystals to a reduced pressure at 0 to 50° C., preferably 10 to 30° C. The pressure in drying may be, for example, less than 200 mmHg, preferably 1 to 50 mmHg. The drying treatment can be monitored by measuring the amount of water in the crystals. Usually, the drying will be completed in 1 to 24 hours.

A freeze-dried preparation of amrubicin hydrochloride can be prepared by dissolving β-type crystalline amrubicin hydrochloride in water, and freeze-drying the dissolved amrubicin hydrochloride. Preferably, a freeze-dried preparation of amrubicin hydrochloride can be prepared by:

(1) dissolving β-type crystalline amrubicin hydrochloride and L-cysteine or a salt thereof in water;

(2) adjusting the pH of the solution to a value of from pH 2 to pH 5; and (3) freeze-drying the dissolved amrubicin hydrochloride. Specifically, a freeze-dried preparation of amrubicin hydrochloride can be prepared by the method described in Japanese Patent 2,603,480 and U. S. Pat. No. 4,952,566, but using the β-type crystalline form.

Suitable salts. of L-cysteine include the hydrochloride and sulfate salts. A preferred amount of L-cysteine or a salt thereof may be, for example, 0.1 to 50 mg, more preferably 0.6 to 9 mg, to every 20 mg of β-type crystalline amrubicin hydrochloride. The pH of the solution of β-type crystalline amrubicin hydrochloride and L-cysteine or a salt thereof is preferably adjusted to a value of from pH 2 to pH 5, more preferably from pH 2.5 to pH 3.5. Alkaline hydroxides or carbonates such as sodium hydroxide and sodium carbonate and inorganic acids such as hydrochloric acid and sulfuric acid may be added as a pH adjusting agent.

The thus-obtained, pH-adjusted solution may be subjected to further process steps such as sterile filtration if desired, and is then filled into vials, and subjected to freeze-drying to prepare a powdered freeze-dried preparation of amrubicin hydrochloride.

Additives such as conventional excipients may be added before, during or after freeze-drying if desired.

The freeze-dried preparation of amrubicin hydrochloride can be dissolved in a suitable solvent such as water for injection just before it is applied as injection or another preparation.

The present invention will be described in detail below, referring to Examples, which are not limitative of the present invention.

EXAMPLE 1
β-Type crystalline amrubicin hydrochloride

1N Hydrochloric acid (2.05 g) and acetic acid (0.75 g) were added to a solution of amrubicin (1.0 g) in water (10 g) and acetone (6.7 g) at 0 to 5° C., to adjust the pH to 2.5, and stirred for 30 minutes. The reaction mixture was poured into acetone (280 g) at 30 to 34° C., and stirred for 3 hours. The precipitated crystals were collected by filtration, and washed with acetone (9.8 g) to give wet crystals of amrubicin hydrochloride. The wet crystals were added again to mixture of acetone (280 g) and water (11.8 g), and stirred at 30 to 34° C. for 1 hour. The crystals were collected by filtration, and washed with acetone (9.8 g), and dried under reduced pressure at room temperature.

Next, the acetone in the crystals was removed by allowing the crystals to stand in a vacuum desiccator together with a piece of wet filter paper at room temperature under a pressure of 50 mmHg for 8 hours, to moisten the crystals. Then, the crystals were allowed to stand in a vacuum desiccator at room temperature under a pressure of 10 mmHg, to give the β-type crystalline amrubicin hydrochloride (1.02 g).

EXAMPLE 2
β-Type crystalline amrubicin hydrochloride

1N Hydrochloric acid (3.65 g) and acetic acid (1.31 g) were added to a solution of amrubicin (1.5 g) in water (15 g) and acetonitrile (10.1 g) at 0 to 5° C., to adjust the pH to 2.5, and stirred for 30 minutes. The reaction mixture was poured into acetonitrile (420 g) at 30 to 34° C., and seed crystals of β-type crystalline amrubicin hydrochloride (3 mg) were added thereto, and stirred for 3 hours. The crystals formed were collected by filtration, and washed with acetonitrile to give wet crystals of amrubicin hydrochloride, which were dried under reduced pressure at room temperature.

Then the acetonitrile in the crystals was removed in a manner similar to that of Example 1, to give the β-type crystalline amrubicin hydrochloride (1.44 g).

EXAMPLE 3
β-Type crystalline amrubicin hydrochloride

Example 2 was repeated exactly except that isopropanol (420 g) was used in place of acetonitrile in the crystallization step and isopropanol was used in place of acetonitrile in washing step.

Then the isopropanol in the crystals was removed in a manner similar to that of Example 1, to give the β-type crystalline amrubicin hydrochloride (1.17 g).

Reference example 1
Another form of crystalline amrubicin hydrochloride

Example 1 was repeated exactly except that the reaction mixture was poured into acetone at 10 to 14° C. instead of 30 to 34° C.

Then the acetone in the crystals was removed in a manner similar to that of Example 1, to give another form of crystalline amrubicin hydrochloride (1.07 g), which is referred to as "α-type crystalline amrubicin hydrochloride" hereinafter.

EXAMPLE 4
Powder X-ray diffraction spectrum of crystalline amrubicin hydrochlorides Powder X-ray diffraction spectra were measured using 1.541Å of Cu·K α with the X-ray diffraction spectrometer RINT 2500V (Rikagaku Electric Co. Ltd.).

The average values of diffraction angles and the relative intensities in the powder X-ray diffraction spectrum of β-type crystalline amrubicin hydrochloride obtained in Example 1 are given above in Table 1. The powder X-ray diffraction spectrum is shown in FIG. 1.

The powder X-ray diffraction spectrum of α-type crystalline amrubicin hydrochloride obtained in Reference example 1 is shown in FIG. 2.

The average values of the diffraction angle has normal precision, for example, about ±0.1. The relative intensity also has normal precision.

EXAMPLE 5
Preservation stability of crystalline amrubicin hydrochlorides

β-Type crystalline amrubicin hydrochloride obtained in Example 1 and α-type crystalline amrubicin hydrochloride obtained in Reference example 1 were each kept at a temperature of 80° C. for 24 hours. Thereafter, the remaining amount of crystals were measured using high performance liquid chromatography. The amount at the starting time is defined as 100%. The results are shown in Table 2

TABLE 2

| amrubicin hydrochloride | remaining amount (%) |
| --- | --- |
| β-type crystalline | 100.4 |
| α-type crystalline | 92.2 |

The results indicate that β-type crystalline amrubicin hydrochloride of the present invention has higher thermal stability than α-type crystalline amrubicin hydrochloride.

EXAMPLE 6
Freeze-dried preparation of amrubicin hydrochloride

β-Type crystalline amrubicin hydrochloride obtained in Example 1 (20 mg), L-cysteine hydrochloride monohydrate (12 mg) and lactose (50 mg) were dissolved in distilled water for injection (10 ml) at 0 to 5° C. A small amount of sodium hydroxide and hydrochloric acid were added thereto until the pH was adjusted to about 2.5. Then the mixture was sterilely filtered and filled into vials (18 ml each), which were then subjected to freeze-drying and sealed with rubber stoppers to obtain a freeze-dried preparation of amrubicin hydrochloride.

EXAMPLE 7
Freeze-dried preparation of amrubicin hydrochloride

β-Type crystalline amrubicin hydrochloride obtained in Example 1 (20 mg), L-cysteine hydrochloride monohydrate (3.2 mg) and lactose (50 mg) were dissolved in distilled water for injection (10 ml) at 0 to 5° C. A small amount of sodium hydroxide was added thereto until the pH was adjusted to about 3.0. Then the mixture was sterilely filtered and filled into vials (18 ml each), which were then subjected to freeze-drying and sealed with rubber stoppers to obtain a freeze-dried preparation of amrubicin hydrochloride.

What is claimed is:

1. A crystalline amrubicin hydrochloride having a powder X-ray diffraction pattern having average values of diffraction angle(2 θ) and relative intensity as given in the following table

| diffraction angle(2θ) (average value) | relative intensity(%) (average value) |
|---|---|
| 6.3 | 100 |
| 6.7 | 56 |
| 10.1 | 44 |
| 15.3 | 36 |
| 20.3 | 56 |
| 25.6 | 37 |
| 26.5 | 61 |
| 26.9 | 52 |

2. A process of preparing a crystalline amrubicin hydrochloride according to claim 1 comprising crystallizing amrubicin hydrochloride at a temperature of 15° C. or above.

3. A process according to claim 2 comprising crystallizing amrubicin hydrochloride from a mixture of (a) hydrophilic organic solvent and (b) a solution of amrubicin hydrochloride in water or a mixture of water and hydrophilic organic solvent, at a temperature of 15° C. or above.

4. A process according to claim 2 comprising:
   (1) dissolving amrubicin hydrochloride in water or a mixture of water and hydrophilic organic solvent;
   (2) adjusting the pH of the solution to a value of from pH 1.5 to pH 4;
   (3) crystallizing amrubicin hydrochloride by adding the solution to hydrophilic organic solvent at a temperature of 15° C. to 50° C.

5. A process according to claim 2, wherein the crystallization temperature is 22° C. to 40° C.

6. A process according to claims 3, wherein the hydrophilic organic solvent (a) is acetone, isopropanol or acetonitrile.

7. A process of preparing a freeze-dried preparation of amrubicin hydrochloride, comprising dissolving crystalline amrubicin hydrochloride according to claim 1 in water, and freeze-drying the dissolved amrubicin hydrochloride.

8. A process according to claim 7 comprising:
   (1) dissolving crystalline amrubicin hydrochloride according to claim 1 and L-cysteine or a salt thereof in water;
   (2) adjusting the pH of the solution to a value of from pH 2 to pH 5; and
   (3) freeze-drying the dissolved amrubicin hydrochloride.

9. A crystalline amrubicin hydrochloride according to claim 1 for use in the treatment of the human or animal body by therapy.

10. A pharmaceutical composition comprising a crystalline amrubicin hydrochloride according to claim 1 and a pharmaceutically acceptable carrier.

11. A method of treating cancer comprising administrating to a person in need thereof, a freeze-dried preparation of amrubicin hydrochloride prepared according to claim 7.

12. A method of treating cancer comprising administrating to a person in need thereof, a pharmaceutical composition according to claim 10.

* * * * *